United States Patent
Miller et al.

(10) Patent No.: US 8,338,398 B2
(45) Date of Patent: Dec. 25, 2012

(54) COMPOSITION AND METHOD OF TREATING HEARING LOSS

(75) Inventors: Josef Miller, Ann Arbor, MI (US);
Colleen LePrell, Ypsilanti, MI (US);
Jochen Schact, Ann Arbor, MI (US);
Diane Prieskorn, Livonia, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/091,931

(22) Filed: Apr. 21, 2011

(65) Prior Publication Data

US 2011/0280964 A1 Nov. 17, 2011

Related U.S. Application Data

(63) Continuation of application No. 11/623,888, filed on Jan. 17, 2007, now Pat. No. 7,951,845.

(60) Provisional application No. 60/760,055, filed on Jan. 19, 2006.

(51) Int. Cl.
*A61K 33/06* (2006.01)
*A61K 31/355* (2006.01)
*A61K 31/60* (2006.01)
*A61K 31/07* (2006.01)
*A61K 31/375* (2006.01)
*A61K 31/245* (2006.01)

(52) U.S. Cl. ........ 514/171; 514/733; 514/458; 514/725; 514/474; 424/682

(58) Field of Classification Search ............... 514/458, 514/474, 725, 733, 171; 381/60; 424/682
See application file for complete search history.

(56) References Cited

U.S. PATENT DOCUMENTS 6,524,619 B2 * 2/2003 Pearson et al. ............... 424/472

* cited by examiner

*Primary Examiner* — Sreeni Padmanabhan
*Assistant Examiner* — Sahar Javanmard
(74) *Attorney, Agent, or Firm* — Howard & Howard Attorneys PLLC (57) ABSTRACT

A composition for treating hearing loss includes components that function through different biological mechanisms to provide an additive effect that is equal to or greater than a sum of the effect of the individual components. The composition includes a biologically effective amount of at least one scavenger of singlet oxygen, a donor antioxidant, a third antioxidant, and a vasodilator. A method of treating hearing loss includes the step of internally administering the composition including a biologically effective amount of the at least one scavenger of singlet oxygen, the donor antioxidant, the third antioxidant, and the vasodilator to a mammal within three days of trauma to a middle or inner ear of the mammal.

22 Claims, 3 Drawing Sheets

COMPOSITION AND METHOD OF TREATING HEARING LOSS

RELATED APPLICATIONS

This patent application is a continuation of U.S. patent application Ser. No. 11/623,888, filed on Jan. 17, 2007, which claims priority to and all advantages of U.S. Provisional Patent Application No. 60/760,055, which was filed on Jan. 19, 2006.

GOVERNMENT LICENSE RIGHTS

This invention was made with government support under grant number DC04058 awarded by the National Institute of Health National Institute of Deafness and Other Communication Disorders (NIH-NIDCD). The government has certain rights in the invention

BACKGROUND OF THE INVENTION

1. Field of the Invention

The present invention generally relates to a composition for treating hearing loss. More specifically, the present invention relates to a composition for treating hearing loss that includes components that function through different biological mechanisms and provide an additive effect that is equal to or greater than a sum of the effects of the individual components, and a method of treating hearing loss including the step of administering the composition to a mammal prior to or within 3 days following trauma to the inner ear.

2. Description of the Related Art

Extensive studies have been performed on compositions for treating hearing loss, along with methods of treating hearing loss using various compositions. In particular, antioxidants, among numerous other components, have been found to play a role in the prevention of noise-induced hearing loss. Specific antioxidants shown to be partially effective in reducing noise-induced hearing loss in animal models include glutathione (GSH)/glutathione monoethyl ester, N-acetylcysteine (NAC), resveratrol, allopurinol, R-phenylisopropyladenosine, and vitamins A, C, and E. Otoprotective effects of the above individual dietary antioxidants are well known in the art.

In addition to antioxidants, many other components have separately been investigated and found to be somewhat efficacious in treating hearing loss. Vasodilators are one class of components that have proven moderately useful for preventing hearing loss. It is known in the art that high levels of noise result in a decrease in blood flow to the inner ear, although the mechanism underlying this noise induced decrease has not been clear until very recently. On the basis of the observed decrease, it has long been speculated that this decrease in blood flow may lead to cell death in sensitive hair cells within a cochlea of the ear and accordingly an increase in blood flow may protect the inner ear cells from noise-induced death. Some vasodilators promote increased blood flow to the inner ear and, thus, help to protect the inner ear from trauma as a result of high levels of noise. Specific examples of vasodilators proven to partially prevent hearing loss include magnesium, betahistine, and hydroxyethyl starch (HES).

Figure 1:
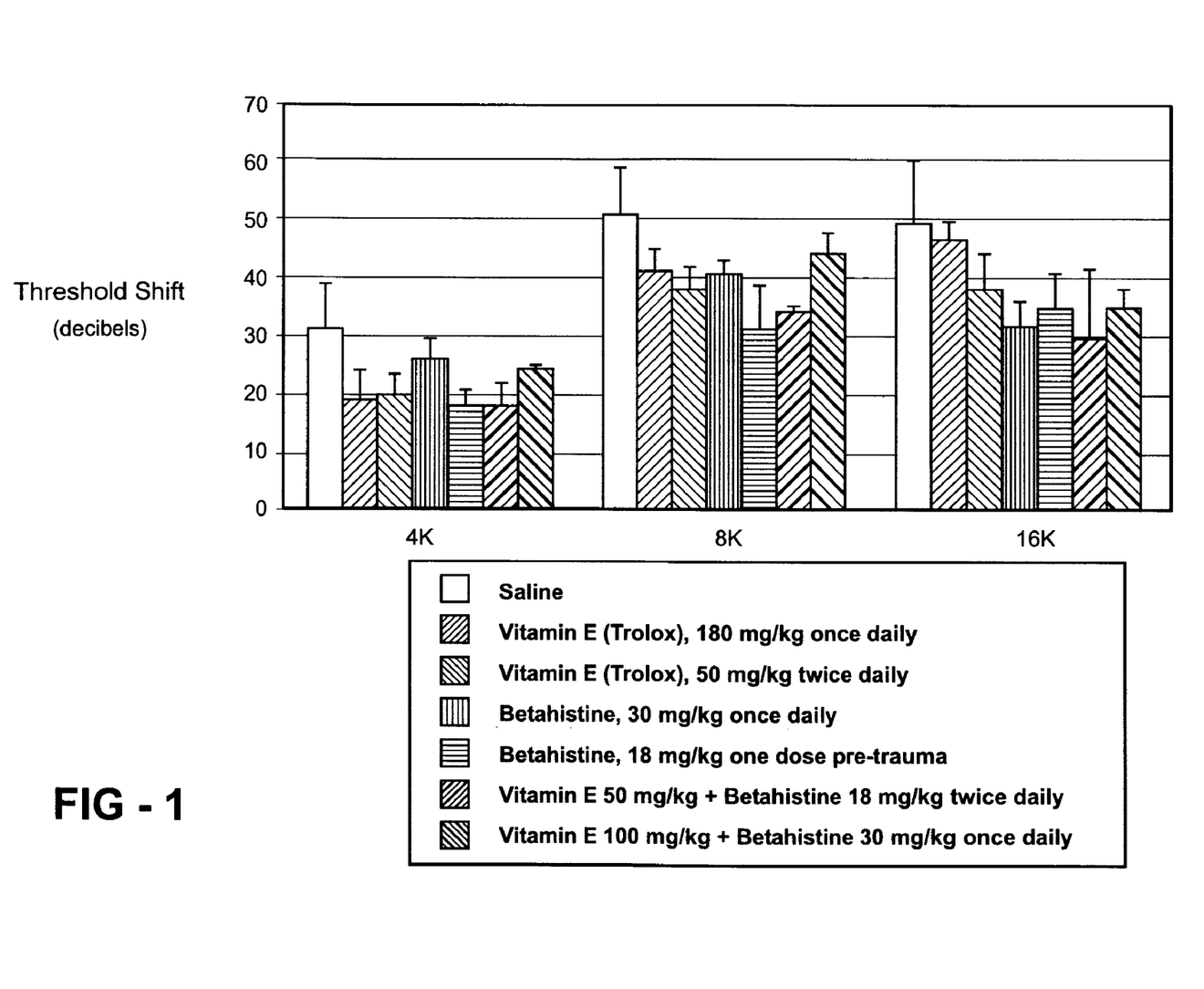
FIG. 1 is a graph showing the effect of a Comparative Example of a composition used to treat hearing loss including Trolox® (vitamin E) and betahistine on reduction of a threshold shift in guinea pigs from baseline threshold sensitivity at 4, 8, and 16 kHz after exposure to 120 decibel SPL Octave Band Noise centered at 4 kHz for five hours.

To date, little, if any, additive effects have been found to exist by combining many of the known components for treating hearing loss. Additive effects, as used herein, refer to effects that are equal to or greater than a sum of the effects of the individual components. For the most part, no greater effect is observed by combining many of the different components that are effective in treating hearing loss than the effect of the most effective individual component in the composition, i.e., combinations of agents are only as effective as the most effective single agent delivered alone. For example, FIG. 1 shows the results of experimentation relative to additive effects of Trolox®, which is a water-soluble analogue of alpha-tocopheral (vitamin E), and betahistine. The experimental conditions are described in further detail in the Examples section below. As is evident from FIG. 1, the combined effect of Trolox® and betahistine in minimizing threshold shift, which correlates to hearing loss, is no greater than the effect of the most effective of either Trolox® or betahistine alone for any given experiment. As such, the combination of Trolox® and betahistine does not produce an additive effect in treating hearing loss.

As the understanding of the mechanisms by which the various antioxidants work to treat or prevent hearing loss has become clearer, it has been found that combinations of certain antioxidants that act via complementary, but different, biochemical mechanisms may be more effective than the individual antioxidants alone. However, given the volume and variety of components that are known to affect hearing loss, as well as lack of knowledge relative to specific mechanisms by which the components function, additive effects between components have not been recognized to date.

In spite of the fact that additive effects between various components have not been recognized to date, certain disclosures have been made that generally group together all known components for treating hearing loss. These disclosures do not teach with sufficient specificity combinations of specific components that exhibit additive effects in treating hearing loss. For example, U.S. Pat. No. 6,093,417 is directed to a composition to treat ear disorders. The composition is topically applied into an ear canal to treat the hearing disorder. Although the U.S. Pat. No. 6,093,417 is directed to a composition that may include many components that are known to be somewhat effective in reducing hearing loss alone, including vitamins A, C, and E along with vasodilators and magnesium salts, there is no recognition of an additive effect between any of the components. As is evident from the above description relative to FIG. 1, many combinations of components do not exhibit additive effects. As such, the random combination of agents disclosed in the U.S. Pat. No. 6,093,417 would not necessarily be expected to provide any greater effect for treating hearing loss if included in the composition. Furthermore, effectiveness of the individual components greatly varies between oral, intravenous, and topical administration, and compositions for treating hearing loss are formulated differently depending on the contemplated mode of administration. Finally, the U.S. Pat. No. 6,093,417 does not teach with sufficient specificity biologically effective amounts of each component that would be sufficient to produce an effect individually, let alone additive effects between the various components. Thus, the disclosure of the U.S. Pat. No. 6,093,417 provides no further teaching than what was already known about each of the components, i.e., that each component, when used individually, is modestly effective in preventing hearing loss.

Although many of the components that are used to treat or prevent hearing loss provide other beneficial functions and are included in multivitamins, known multivitamins do not include biologically effective amounts of the components sufficient to treat or prevent hearing loss. Furthermore, multivitamins are generally used as part of a regular dietary regimen and there is no data that suggests the use of multivitamins that include a specific combination and concentration of components to prevent hearing loss induced by noise or other stress.

The use of dietary antioxidants to prevent visual dysfunction is disclosed in U.S. Pat. No. 6,660,297. The U.S. Pat. No. 6,660,297 patent specifically discloses vitamins A, C, and E in amounts that may be biologically effective to treat or prevent hearing loss. However, a combination of vitamins A, C, and E alone is not sufficient to yield clinically significant protection against noise induced hearing loss and the addition of zinc and copper as disclosed in the U.S. Pat. No. 6,660,297 patent would not be expected to reduce hearing loss. Furthermore, there is no suggestion or teaching in the U.S. Pat. No. 6,660,297 patent to use the composition for anything other than treating visual dysfunction.

Thus, there is an opportunity to provide a composition and a method of treating hearing loss including the step of administering the composition that includes a specific combination of components having an additive effect that is equal to or greater than the sum of the effect of the individual components in treating hearing loss when used in biologically effective amounts.

SUMMARY OF THE INVENTION AND ADVANTAGES

The subject invention provides a composition for treating hearing loss including components that function through different biological mechanisms to provide an additive effect that is equal to or greater than a sum of the effect of the individual components. The composition includes a biologically effective amount of at least one scavenger of singlet oxygen, a donor antioxidant, a third antioxidant, and a vasodilator. The at least one scavenger of singlet oxygen is present for reducing free radicals that contribute to hearing loss. The donor antioxidant is present for reducing peroxyl radicals and inhibiting propagation of lipid peroxidation that also contributes to hearing loss. The vasodilator is present for preventing decreases in both cochlear blood flow and oxygenation that also contribute to hearing loss.

The subject invention also provides a method of treating hearing loss. The method includes the step of internally administering the composition of the subject invention including a biologically effective amount of the at least one scavenger of singlet oxygen, the donor antioxidant, the third antioxidant, and the vasodilator to a mammal within three days of trauma to a middle or inner ear of the mammal.

The combination of at least one scavenger of singlet oxygen, the donor antioxidant, the third antioxidant, and the vasodilator, in the biologically effective amounts, provides an additive effect in treating hearing loss that is equal to or greater than a sum of the effect of the individual components. Even more, the composition of the subject invention should prove to be effective in treating hearing loss if administered as late as three days after trauma to the middle or inner ear of the mammal. As a result, the composition and method of treating hearing loss of the subject invention provide great promise in helping to minimize hearing loss resulting from trauma to middle or inner ears of mammals. Given the high incidence of noise-induced hearing loss in the general population worldwide, there is a great need for the composition and method of treating hearing loss of the subject invention in order to minimize socioeconomic effects that persist due to noise-induced hearing loss.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE PREFERRED EMBODIMENT

A composition for treating hearing loss includes components that function through different biological mechanisms to provide an additive effect that is equal to or greater than a sum of the effect of the individual components. The composition is typically used for treating hearing loss resulting from trauma to a middle or inner ear of a mammal. The trauma may be further defined as mechanically-induced metabolic trauma, mechanical/metabolic trauma, stress trauma, stress-induced damage, or environmental stress. However, it is also possible that the composition may also be used to treat or prevent other types of hearing loss, including, for example, age-related hearing loss, antibiotic-induced hearing loss, and chemotherapeutic-induced hearing loss. The composition may further be used to prevent hearing loss during restoration surgery performed on the middle or inner ear.

It has been found that one result of noise trauma, or other stressors such as age and drugs as listed above, is that free radicals form in association with metabolic trauma. The free radicals damage sensitive structures, such as hair cells, within the ear. Vasoconstriction also occurs as a result of the noise, which leads to decreased blood flow to the middle and inner ear and causes cell death that results in hearing loss. It has been found that the underlying cause of vasoconstriction is noise-induced free radical formation. Specifically, one of the molecules formed in the inner ear as a result of the presence of free radicals is 8-isoprostane-2F alpha, which is a bioactive agent. The bioactive agent induces a constriction of blood vessels in the inner ear, which causes a reduction in blood flow. In order to counteract the free radical formation and the vasoconstriction, the composition of the subject invention includes at least one scavenger of singlet oxygen, a donor antioxidant, a third antioxidant, and a vasodilator. Unexpectedly, it was found that the composition including the at least one scavenger of singlet oxygen, the donor antioxidant, the third antioxidant, and the vasodilator produce the additive effect that is not only greater than the effect of any one of those components alone, but at least equal to or greater than a sum of the effects of each of the components.

Antioxidants act through a variety of mechanisms. The at least one scavenger of singlet oxygen and the donor antioxidant are two different classes of antioxidants that act through different mechanisms. The third antioxidant, while typically a scavenger of singlet oxygen, may be a different antioxidant that acts through a different mechanism. Scavengers of singlet oxygen reduce free radicals that contribute to hearing loss. More specifically, by reducing free radicals, the scavengers of singlet oxygen prevent, among other damaging effects, the singlet oxygen from reacting with lipids to form lipid hydroperoxides. Lipid hydroperoxides play a role in causing hearing loss.

Even within the class of scavengers of singlet oxygen, it is believed that various antioxidants react at different sites within the body, and in particular, within cells to attenuate free radical formation. For example, one of the scavengers of singlet oxygen is typically vitamin A. Vitamin A is a generic term that captures a number of molecules with a biological activity of retinol or carotenoids. Primary dietary forms of vitamin A/retinol include retinol esters and beta-carotene. The beta-carotene is made up of a polyene chain of 11 conjugated double bonds with methyl branches spaced along the polyene chain, capped at both ends by cyclohexenyl rings with 1,1,5-trimethyl substitution. Other forms of vitamin A include xanxthophylls, astaxanthin, canthxanxin, lutein, and zeaxanthin, which include a backbone of beta-carotene with hydroxyl and/or carbonyl substitution on one or more of the cyclohexenyl rings. For purposes of the subject invention, the vitamin A is typically present as beta-carotene. Beta-carotene is a powerful scavenger of singlet oxygen, as well as nitric oxide and peroxynitrite, and may also scavenge lipid peroxyl radicals within a lipophilic compartment of a mitochondrial membrane. Beta-carotene is an excellent scavenger of free radicals under normal physiological conditions present in most tissues.

In addition to vitamin A, other scavengers of singlet oxygen may also be present in the composition of the subject invention. For example, another scavenger of singlet oxygen that may be present is resveratrol. Resveratrol is more efficient at scavenging hydroxyl radicals than vitamin C, and the addition of resveratrol to the vitamins A may have additive effects. The use of resveratrol in combination with other antioxidants (but not vitamins A, C, or E, and not the vasodilator magnesium or any other vasodilating substance), is known in the art to reduce age-related hearing loss.

The at least one scavenger of singlet oxygen is present in the composition in a biologically effective amount. For purposes of the subject invention, the biologically effective amount is further defined as an amount that is sufficient to produce an additive effect in a reduction in threshold shift when used in combination with other antioxidants and the magnesium. Additive effect, as used herein, refers to an effect that is equal to or greater than a sum of the effects of the individual components. In order to produce the additive effect, the at least one scavenger of singlet oxygen is typically present in the composition in a total amount of at least 830 international units (IU), more preferably from 830 to 120,000 IU, most preferably from about 2,100 to 70,000 IU for an adult dosage.

The amount of the vitamin A present in the composition is dependent upon the form of vitamin A that is used. For example, in one embodiment, vitamin A is present as retinol in an amount of at least 830 IU, more preferably from 830 to 10,000 IU, most preferably from 2,100 to 5,900 IU. As known in the art, a conversion of IU to weight for vitamin A is 3.33 IU/µg. Thus, at least 830 international units (IU) is equivalent to at least 0.25 mg of vitamin A, from 830 to 10,000 IU of vitamin A is equivalent to from 0.25 to 3 mg of vitamin A, and from 2,100 to 5,900 IU of vitamin A is equivalent to from 0.62 to 1.8 mg vitamin A.

Alternatively, the vitamin A may be present in the composition as beta-carotene, as opposed to retinol. The retinol activity equivalents (RAE) for retinol conversion to beta-carotene, which is a pro-vitamin A carotenoid, is 1 mg to 12 mg. In terms of conversion of the amounts set forth above for the vitamin A present in the composition as retinol to the vitamin A present in the composition as beta-carotene, a total amount of at least 3.0 mg or at least 10,000 international units (IU) of vitamin A as beta-carotene, more preferably from 3.0 to 36 mg or 10,000 to 120,000 IU vitamin A as beta-carotene, most preferably from about 7.5 to 21 mg or 25,000 to 70,000 IU of vitamin A as beta-carotene is typically present for an adult dosage.

Specific amounts of the vitamin A present in the composition may be dependent on the body weight of the mammal. In one specific example, the amount of vitamin A present as retinol in the composition is about 0.0178 mg/kg body weight. Thus, for an average human weighing about 70 kg, the amount of vitamin A present as retinol in the composition may be about 1.25 mg, or if the vitamin A is in the form of beta-carotene, the beta carotene may be present in an amount of about 15 mg.

It is to be appreciated that, when additional scavengers of singlet oxygen such as resveratrol are present in the composition in addition to vitamin A, the total amount of scavengers of singlet oxygen may be greater than the ranges set forth above for the at least one scavenger of singlet oxygen, so long as at least one scavenger of singlet oxygen is present in the amounts set forth above. In addition, other scavengers of singlet oxygen may be used in place of vitamin A, so long as the amount of the at least one scavenger of singlet oxygen is present within the amounts set forth above. When present, the resveratrol is typically included in the composition in an amount of at least 1 mg, more typically in an amount of from 10 mg to 1500 mg, most typically in an amount of from 15 mg to 1000 mg.

Whereas the at least one scavenger of singlet oxygen prevents the initial formation of lipid peroxides, the donor antioxidant reduces peroxyl radicals and inhibits propagation of lipid peroxidation that contributes to hearing loss. More specifically, the donor antioxidant reacts with and reduces peroxyl radicals and thus serves a chain-breaking function to inhibit propagation of lipid peroxidation. As is evident from the chain-breaking function of the donor antioxidant in lipid peroxidation, the donor antioxidant functions within cell membranes. A specific donor antioxidant that is contemplated for use in the composition of the subject invention is vitamin E. Vitamin E is a generic term for all tocols and tocotrienol derivatives with a biological activity of alpha-tocopherol. Primary dietary forms of vitamin E include vitamin E itself and alpha-tocopherol. Trolox®, a water-soluble analogue of alpha-tocopheral commercially available from Hoffman-Laroche, Ltd. of Basel, Switzerland, is a research agent that is typically used as a source of vitamin E.

The donor antioxidant is typically present in the composition in an amount of at least 75 IU, more preferably from 75 IU to 1500 IU, most preferably from 150 IU to 800 IU. As known in the art, a conversion of IU to weight for vitamin E is 0.66 mg/IU. Thus, when the donor antioxidant is vitamin E, at least 75 IU of vitamin E is equivalent to at least 50 mg of vitamin E, from 75 to 1500 IU of vitamin E is equivalent to from 50 to 1000 mg of vitamin E, and from 150 to 800 IU of vitamin E is equivalent to from 150 to 600 mg of vitamin E. As with the amount and type of vitamin A, specific amounts of the vitamin E present in the composition may be dependent on the body weight of the mammal. In one specific example, the amount of vitamin E present in the composition is about 2.6 mg/kg body weight. Thus, for an average human weighing about 70 kg, the amount of vitamin E present in the composition may be about 182 mg.

In addition to the at least one scavenger of singlet oxygen and the donor antioxidant, the composition further includes the third antioxidant. While the third antioxidant may be a scavenger of singlet oxygen, the third antioxidant may also be an antioxidant that functions through a different mechanism. When the third antioxidant is a scavenger of singlet oxygen, the at least one scavenger of singlet oxygen is still present in the composition as a separate component from the third antioxidant, and is still present in the composition in the amounts set forth above for the at least one scavenger of singlet oxygen. As a result of the third antioxidant being another scavenger of singlet oxygen, the resulting composition would have at least two scavengers of singlet oxygen.

The third antioxidant is typically vitamin C, which is a scavenger of singlet oxygen and reactive nitrogen species. It is to be appreciated that, although the third antioxidant is typically vitamin C, other antioxidants may be used in place of the vitamin C, and the other antioxidants may function through different mechanisms than vitamin C. The term vitamin C applies to substances that possess antiscorbutic activity and includes two compounds and their salts: L-ascorbic acid (commonly called ascorbic acid) and L-dehydroascorbic acid. In addition to being known as ascorbic acid and L-ascorbic acid, vitamin C is also known as 2,3-didehydro-L-threo-hexano-1,4-lactone, 3-oxo-L-gulofuranolactone, L-threo-hex-2-enonic acid gamma-lactone, L-3-keto-threo-hexuronic acid lactone, L-xylo-ascorbic acid and antiscorbutic vitamin. Vitamin C is known to scavenge both reactive oxygen species and reactive nitrogen species. It can be oxidized by most reactive oxygen and nitrogen species, including superoxide, hydroxyl, peroxyl and nitroxide radicals, as well as such non-radical reactive species as singlet oxygen, peroxynitrite and hypochlorite. Vitamin C thus inhibits lipid peroxidation, oxidative DNA damage, and oxidative protein damage.

In contrast to vitamin A, which functions best under conditions present in most tissues, water-soluble vitamin C is an excellent free radical scavenger in an aqueous phase to thus reduce free radicals at a site different from that of vitamin A. More specifically, ascorbic acid functions to reduce free radicals in fluid, such as in cytoplasmic fluid and/or blood, before the free radicals reach cell membranes.

The third antioxidant is typically present in an amount of at least 4,000 IU, more preferably from 6,000 to 40,000, most preferably from 8,000 to 20,000 IU. Using vitamin C as an example for converting IU to weight units for the third antioxidant, as known in the art, a conversion of IU to weight for vitamin C is 0.05 mg/IU. Thus, at least 4,000 IU of vitamin C is equivalent to at least 200 mg of vitamin C, from 6,000 to 40,000 IU of vitamin C is equivalent to from 300 to 2,000 mg vitamin C, and from 8,000 to 20,000 IU vitamin C is equivalent to from 400 to 1,000 mg vitamin C. As with vitamins A and E, specific amounts of the vitamin C or other third antioxidant present in the composition may be dependent on the body weight of the mammal. In one specific example, the amount of vitamin C present in the composition is about 7.14 mg/kg body weight. Thus, for an average human weighing about 70 kg, the amount of vitamin C present in the composition may be about 500 mg.

As set forth above, the composition further includes a vasodilator. Typically, the vasodilator includes magnesium; however, the vasodilator, for purposes of the subject invention, may include other vasodilators in place of or in addition to the magnesium, or may include only magnesium. Vasodilators are known in the art for use in preventing hearing loss. Vasodilators including magnesium prevent decreases in cochlear blood flow and oxygenation via biochemical mechanisms involving changes in calcium concentration and prostaglandins. Deficient cochlear blood flow and lack of oxygenation are factors that contribute to hearing loss by causing cell death in sensitive hair cells within a cochlea of the ear. Vasodilators including magnesium have also been found to improve the efficacy of immunosuppressant therapy or carbogen inhalation therapy in recovery from sudden hearing loss. Furthermore, it has been found that magnesium deficiency leads to increased calcium channel permeability and greater influx of calcium into cochlear hair cells, increased glutamate release, and auditory nerve excitotoxicity, each of which play a role in health of the middle and inner ear. Although the vasodilators are known in the art for treating hearing loss, the vasodilators, especially magnesium, exhibit an unexpected additive effect when combined with the biologically effective amounts of the at least one scavenger of singlet oxygen, the donor antioxidant, and the third antioxidant, especially when the at least one scavenger of singlet oxygen is vitamin A, the donor antioxidant is vitamin E, and the third antioxidant is vitamin C. The additive effect is greater than not only the most efficacious of the components for treating hearing loss, but typically greater than the sum of the effects of each of the components for treating hearing loss. While vasodilators other than magnesium are envisioned for purposes of the present invention, additive effects are not observed with all vasodilators. For example, betahistine, which is another known vasodilator, does not exhibit an additive effect as is evident from FIG. 1. Specific effects of the composition of the subject invention on treating hearing loss are described in further detail below.

The vasodilator including magnesium typically includes a magnesium salt or magnesium salt complex and, more specifically, magnesium sulfate or magnesium citrate. Other vasodilators including magnesium that may be suitable for purposes of the subject invention include; magnesium acetate, magnesium aspartate, magnesium carbonate, magnesium chloride, magnesium fumarate, magnesium gluconate, magnesium glycinate, magnesium hydroxide, magnesium lactate, magnesium oxide, magnesium salicylate, magnesium stearate, and magnesium sulfate. Other representative salts include but are not limited to; hydrobromide, hydrochloride, bisulfate, nitrate, arginate, ascorbate, oxalate, valerate, oleate, palmitate, laurate, borate, benzoate, phosphate, tosylate, maleate, fumarate, succinate, taurate, tartrate, naphthylate mesylate, glucoheptonate, lactobionate and laurylsulphonate salts.

Typically, the vasodilator is present in the composition in an amount of at least 50 mg. For example, when the vasodilator is magnesium, the magnesium is typically present in an amount of from 50 to 450 mg, most preferably from 100 to 350 mg. As with vitamins A, C, and E, specific amounts of the vasodilator present in the composition may be dependent on the body weight of the mammal. In one specific example, the amount of the vasodilator including magnesium present in the composition is about 2.14 mg/kg body weight. Thus, for an average human weighing about 70 kg, the amount of the vasodilator including magnesium present in the composition may be about 150 mg.

Amounts of the typical components included in the composition, along with more and most preferred amounts, are summarized in Table 1 below.

TABLE 1

| Component | | Amount | More Preferred Amount | Most Preferred Amount | Typical Dosage, mg/kg body weight |
|---|---|---|---|---|---|
| Vitamin A | | ≧830 IU | 830-120,000 IU | 2100-70,000 IU | — |
| | Vitamin A As Retinol | ≧830 IU | 830-10,000 IU | 2,100-5,900 IU | 0.0178 mg/kg |
| | Vitamin A As beta-carotene | ≧10,000 IU | 10,000-120,000 IU | 25,000-70,000 IU | 0.214 mg/kg |
| Vitamin C | | ≧4,000 IU | 6,000-40,000 IU | 8,000-20,000 IU | 7.14 mg/kg |
| Vitamin E | | ≧75 IU | 75-1500 IU | 150-800 IU | 2.6 mg/kg |
| Magnesium | | ≧50 mg | 50-450 mg | 100--350 mg | 2.14 mg/kg |

Although no human experimentation has been performed to date, the amounts specified for the antioxidants and the vasodilator correlate, in terms of biological effectiveness, to amounts used in animal studies on guinea pigs. Furthermore, it is to be appreciated that the biologically effective amounts of the antioxidants and vasodilator may be lower within the above ranges for children than for the average human, based on lower US recommended daily allowances and maximum intake levels for children. This is evident based on the typical dosages in Table 1 based on mg/kg.

In addition to the antioxidants and vasodilator, other components may also be present in the composition for treating hearing loss. For example, in one embodiment, the composition further includes a withanolide. Withanolides have been suggested for use in anti-inflammatory, anti-tumor, cytotoxic, and immunological applications. One example of a specific withanolide that may be included in the composition of the subject invention is the withanolide extracted from day lily plants. The extract is a powerful natural antioxidant which may be effective in preventing cell death in the inner ear by interrupting the cell-death pathway initiated by deafferentation of the auditory nerve. When included in the composition, the withanolide may be present in an amount of at least 10 ppm, more preferably from 10 to 1000 ppm.

A method of treating hearing loss includes the step of internally administering the composition of the subject invention to a mammal. More specifically, the composition may be orally administered to the mammal, such as in the form of a tablet, liquid, gel, etc. Alternatively, the composition may be intravenously administered to the mammal through an IV or an injection of the composition. The composition may also be locally administered via the round window membrane of the cochlea. As a specific example, the vitamins A, C, and E, the vasodilator including magnesium, and the optional components may be first combined to form the composition, with the composition then administered to the mammal. Alternatively, the vitamins A, C, and E, the vasodilator including magnesium, and the other optional components may be separately administered, in which case the composition forms within the mammal.

For purposes of the subject invention, hearing loss is objectively measured in terms of differences in threshold shift. In guinea pig studies, hearing loss and the efficacy of the composition of the subject invention for treating hearing loss is measured as an average difference in threshold shift from baseline threshold sensitivity at 4, 8, and 16 kHz, as compared to an untreated control, after exposure to 120 decibel SPL Octave Band Noise centered at 4 kHz for five hours. Larger differences in threshold shift correlate to less hearing loss and greater efficacy of the composition for treating hearing loss.

It is has been shown that hair cell loss correlates to threshold shift. For example, in guinea pig ears that recover from temporary threshold shift, morphological damage is limited to tips of stereocilia in a third row of outer hair cells (OHCs) whereas ears from animals with permanent threshold shift have damage to all three rows of OHCs and, in some cases, the inner hair cells (IHCs), with damage throughout the length of the stereocilia as well as the to the body of the hair cell.

The composition of the present invention is administered to the mammal within three days of trauma to a middle or inner ear of the mammal in order to alleviate permanent threshold shift. It is to be appreciated that by administrating the composition within three days of trauma, treatment prior to trauma is also contemplated through the method of the present invention. Data from animal studies indicate that temporary threshold shift measured 24 hours post-trauma is well-correlated with permanent threshold shift. Given the relationship between temporary threshold shift and permanent threshold shift, it is clinically beneficial to reduce temporary threshold shift. As such, the composition is preferably administered within one day of trauma to the middle or inner ear of the mammal. Even so, it is expected that treatment within three days with the composition of the present invention is substantially as effective in minimizing permanent threshold shift as treatment within one day.

Treatment within three days is most appropriate when the mammal has sustained trauma to the middle or inner ear through unexpected loud noise or other trauma. Ideally, the composition is administered to the mammal prior to trauma to the middle or inner ear. Treatment prior to trauma is most feasible when the mammal is preparing for sustaining trauma to the middle or inner ear. For example, the composition may be administered prior to restoration surgery performed on the middle or inner ear. As another example, if a person will be firing a weapon or attending an event such as a rock concert, the person may begin treatment prior to sustaining the trauma to the middle or inner ear to attain the best results.

After initial administration of the composition, the composition is typically administered to the mammal each day for at least five days following the trauma to the middle or inner ear of the mammal. Although excellent results have been achieved through such treatment, it is to be appreciated that other treatment regimens may also prove efficacious for purposes of the present invention.

As described in further detail in the Examples section below, an average difference in threshold shift in mammals from baseline threshold sensitivity at 4, 8, and 16 kHz, as compared to an untreated control, is at least 25 decibels after exposure to 120 decibel SPL Octave Band Noise centered at 4 kHz for five hours. More specifically, the threshold shift in mammals treated with the composition of the present invention is expected to be at least 25 decibels lower than the threshold shift in mammals that are treated with a control saline solution. To obtain those results, the composition is orally administered one hour prior to exposure to the noise and administered again each day for five days subsequent to the exposure to the noise. The threshold shift is measured 10 days after exposure to the noise using auditory brainstem response (ABR) testing. Similar results would be anticipated using other alternative measures of auditory or sensory cell function, such as psychophysical tests or otoacoustic emission measures.

In addition, outer hair cell loss and inner hair cell loss is measured both in the whole cochlea and in a trauma region of the cochlea. After treatment according to the method of the present invention, outer hair cell loss in the whole cochlea is less than 10%, and inner hair cell loss in the whole cochlea is less than 5%. Outer cell hair loss in the trauma region is less than 20%, while inner hair cell loss in the trauma region is less than 10%.

The following example, as presented herein, is intended to illustrate and not limit the invention.

EXAMPLE

The method of treating hearing loss with the composition of the present invention is performed on guinea pigs (NIH outbred strain, 250-350 grams) due to their extensive use in auditory research, including studies on noise-induced hearing loss, and because they provide a model similar to humans in terms of development. Six guinea pigs are subject to treatment with the composition of the present invention. In order to determine efficacy of the composition of the present invention in treating hearing loss, baseline threshold sensitivity of the guinea pigs is measured binaurally using auditory brainstem response testing at 4, 8, and 16 kHz. The guinea pigs are then treated with vitamins A, C, E, and magnesium (referred to in FIG. 2 as "ACEMg") in the amounts shown in Table 2. The amounts shown in Table 2 are approximately 10 times expected human doses based on more rapid metabolism of guinea pigs relative to humans.

TABLE 2

| Component | Parts by Weight |
| --- | --- |
| Vitamin A (beta-carotene) | 2.1 mg/kg p.o. |
| Vitamin C (Ascorbic acid) | 71.4 mg/kg s.c |
| Vitamin E (Trolox ®) | 26 mg/kg s.c. |
| Magnesium (MgSO4) | 2.85 mmol/kg s.c. |

One hour later, the guinea pigs are exposed to 120-dB SPL Octave Band Noise centered at 4 kHz for 5 hours to cause trauma to middle or inner ears of the guinea pigs. The noise is sufficient to cause permanent threshold shift, i.e., permanent hearing loss. The composition of the present invention is administered immediately post-exposure to the noise, and again each day for 5 days after the trauma. Ten days after the trauma, auditory sensitivity is measured using ABR. For ABR testing, the guinea pigs are anesthetized with 40 mg/kg ketamine and 10 mg/kg xylazine and placed on a warm heating pad in a sound attenuated chamber. ABR thresholds are determined at 4, 8 and 16 kHz frequencies. To test for the ABR thresholds, tone bursts 10 ms in duration (0.5 ms rise/fall) are presented at a rate of 17/sec. Up to 1024 responses are collected and averaged for each signal frequency to provide a measure of threshold shift at each frequency. Estimates of permanent hearing loss, shown in FIG. 2 in terms of threshold shift in decibels, are calculated as average threshold shift across ears and across frequencies.

Figure 3:
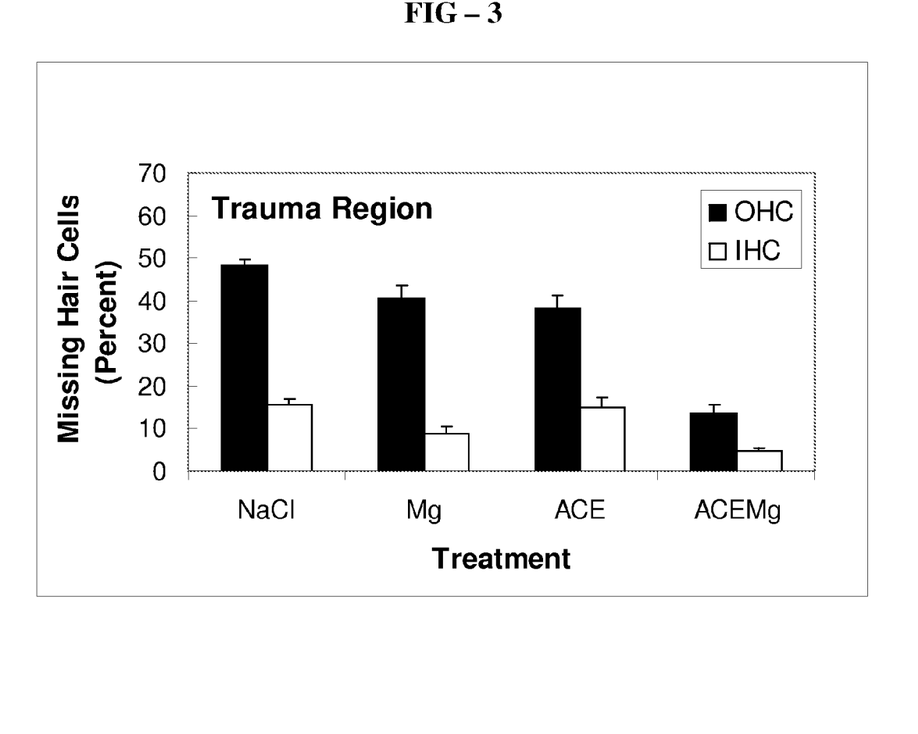
FIG. 3 is a graph showing the effect of the composition of the subject invention and Comparative Examples of compositions of FIG. 2 on an amount of missing hair cells in the region of the cochlea that is most damaged after the noise exposure specified above for FIG. 2.
Figure 4:
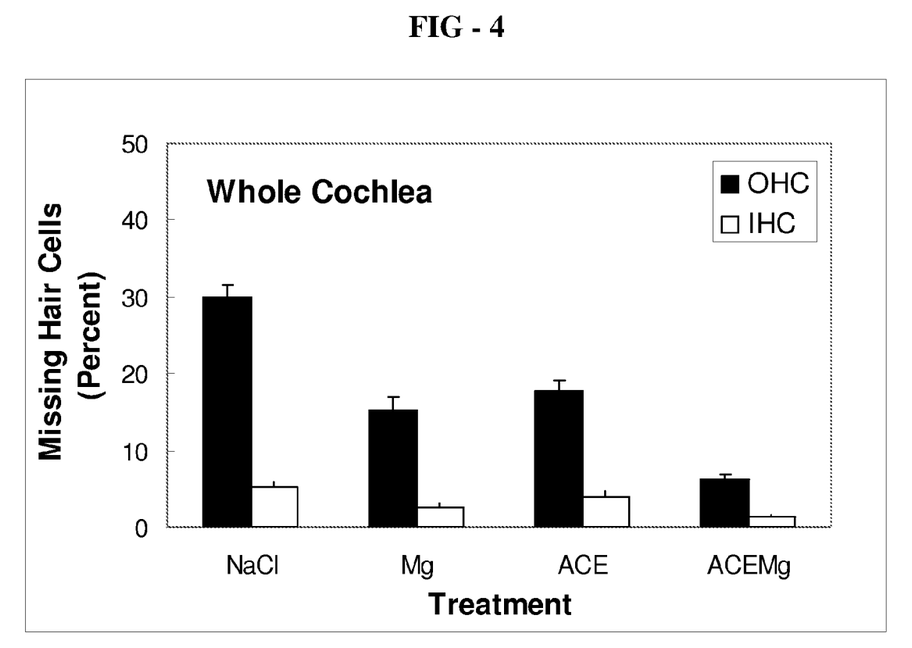
FIG. 4 is a graph showing the effect of the composition of the subject invention and Comparative Examples of compositions of FIG. 2 on an amount of missing hair cells in the whole cochlea after the noise exposure specified above for FIG. 2.

After ABR testing, the guinea pigs are deeply anesthetized and decapitated. Temporal bones are quickly removed, dissected open and fixed with 4% paraformaldehyde. The following day, an otic capsule, lateral wall, and tectorial membrane are removed, and a bony modiolus is carefully detached. Organ of Corti tissue, attached to the modiolus, is permeabilized with 0.3% Triton-X and incubated with rhodamine phalloidin diluted 1:100 in phosphate buffered saline (30 min). After washing the tissues, individual turns from the organ of Corti are dissected, mounted on microscope slides, and examined and photographed using a Leica DMRB epiflourescence microscope. Hair cell counts are conducted, and cytocochleograms are prepared as known in the art. Referring to FIGS. 3 and 4, percentages of missing inner hair cells (IHC) and outer hair cells (OHC) are determined based on the hair cell counts.

Comparative Example 1

Guinea pigs are treated with other compositions in order to compare the efficacy of the composition of the present invention with the other compositions. For example, guinea pigs are separately treated in the same way as specified above in the Example with the following compositions: a saline (NaCl) composition as a control, a composition including only magnesium sulfate (2.85 mmol/kg) as the active ingredient, or a composition including only vitamins A (2.1 mg/kg beta-carotene), C (71.4 mg/kg ascorbic acid), and E (26 mg/kg Trolox®) ("ACE") as the active ingredients. The guinea pigs are subjected to the same ABR testing, and the components of the ear are dissected, as described above in the Example to provide information on threshold shift and hair cell loss. Threshold shift and hair cell loss resulting from treatment with the other compositions are shown in FIGS. 2-4.

Comparative Example 2

Guinea pigs are treated with a composition of vitamin E alone, betahistine alone, or a combination of betahistine and vitamin E to determine if results similar to those achieved with the composition of the present invention including magnesium can be achieved by substituting betahistine for the magnesium. The results of treatment with vitamin E, betahistine, or combination of vitamin E and betahistine are shown in FIG. 1. In one comparative example, guinea pigs are treated once daily with 100 mg/kg vitamin E (Trolox®), 30 mg/kg Betahistine, or a combination of 100 mg/kg Trolox® and 30 mg/kg Betahistine. Five guinea pigs are treated with each of the different compositions. In another comparative example, four guinea pigs are separately treated with 50 mg/kg Trolox® twice daily, 18 mg/kg Betahistine (one dose immediately pre-noise exposure), or a combination of 50 mg/kg vitamin E (Trolox®) and 18 mg/kg Betahistine (N=4 animals per group). Control data are from 18 animals treated with saline delivered either IP (N=11) or IV (N=7). The guinea pigs are subjected to ABR testing, and the components of the ear are dissected, both as described above in the Example, to provide information on threshold shift and hair cell loss.

Figure 2:
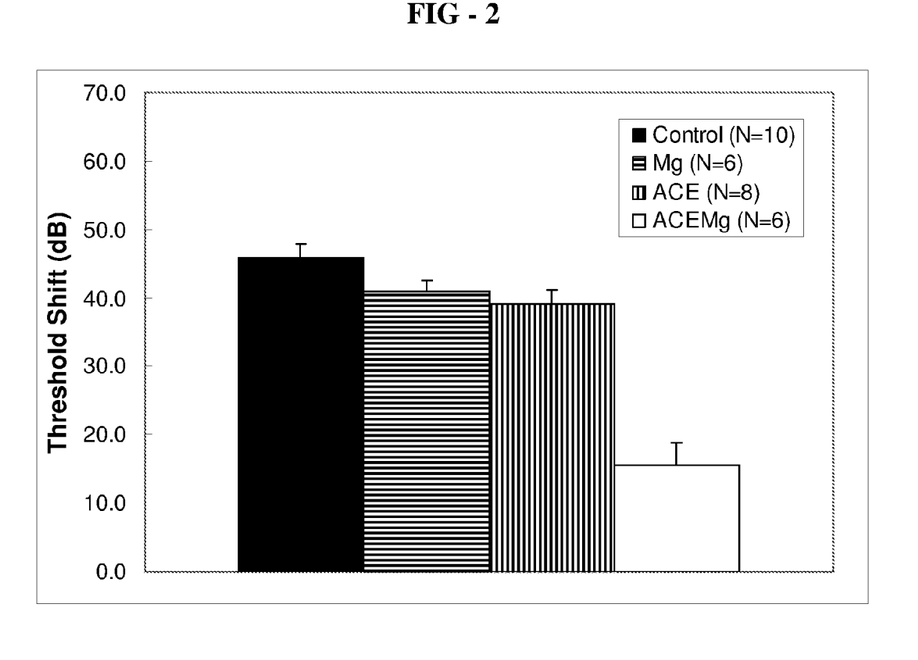
FIG. 2 is a graph showing the effect of a composition of the subject invention including vitamins A, C, and E and magnesium, and comparative examples of compositions that include only some of those components, on average reduction of a threshold shift in guinea pigs from baseline threshold sensitivity at 4, 8, and 16 kHz after exposure to 120 decibel SPL Octave Band Noise centered at 4 kHz for five hours.

Referring to FIGS. 2-4, the effect in treating hearing loss with composition of the present invention including vitamins A, C, E, and magnesium is clearly greater than that associated with the effectiveness of a composition including only magnesium or only vitamins A, C, and E. More specifically, treatment with the composition of the present invention results in a threshold shift of less than 20 decibels, as averaged across all frequencies, while treatment with a control saline solution results in a threshold shift of about 45. As such, a difference in threshold shift between treatment with the composition of the present invention and treatment with the control of saline solution is over 25 decibels. Furthermore, the difference in threshold shift between the composition of the present invention and the control saline solution is greater than the sum of differences in threshold shifts for magnesium or vitamins A, C, and E alone and the control saline solution. Specifically, the sum of the differences in threshold shifts for magnesium and vitamins A, C, and E alone is about 12 decibels. Consistent with the reduction in noise-induced hearing loss, hair cell counts revealed significantly reduced sensory cell death with Mg or A, C, and E, with the greatest protection observed after treatment with vitamins A, C, E, and magnesium. More specifically, less than 10% of outer hair cells and less than 5% of inner hair cells in the whole cochlea are missing after treatment with the composition of the present invention including Mg and vitamins A, C, and E. In the trauma region, less than 20% of outer hair cells and less than 10% of inner hair cells in the whole cochlea are missing after treatment with the composition of the present invention including Mg and vitamins A, C, and E. As shown by FIGS. 3 and 4, the reduction in percentage of missing hair cells after treatment with the composition of the present invention is more than the sum of the reductions in missing hair cells observed when magnesium or vitamins A, C, and E are used alone as compared to the percentage of hair cell loss when saline is used.

Furthermore, as shown in FIG. 1, the Comparative Examples in which vitamin E, betahistine, or a combination of vitamin E and betahistine are used clearly do not exhibit the same additive effect that is observed when magnesium is used as the vasodilator in combination with the vitamins. More specifically, saline treated control animals (white bars) show the greatest hearing loss 10 days post noise. Animals treated with Vitamin E (Trolox: 100 mg/kg once daily or 50 mg/kg twice daily, diagonal lined bars) have less permanent hearing loss than control animals. Animals treated with the vasodilator betahistine (30 mg/kg, once daily, vertical striped bars; or one 18 mg/kg dose pre-noise, horizontal striped bars) show approximately the same amount of protection as those treated with vitamin E. Animals treated with a combination of vitamin E and betahistine (50 mg/kg Trolox twice daily+18 mg/kg betahistine twice daily, or 100 mg/kg Trolox once/daily+30 mg/kg betahistine once/daily; see dark bars with white diagonal hatch) do not have any additive protection beyond that of either single agent alone. As such, not all vasodilators are as effective as magnesium in combination with the vitamins.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A method of treating hearing loss comprising the step of internally administering a composition to a mammal consisting essentially of:
    a biologically effective amount of vitamin A, vitamin E, vitamin C, a vasodilator comprising magnesium, and, optionally, a withanolide, and/or reservatrol,
    wherein the composition is initially administered within three days of trauma to a middle or inner ear of the mammal to provide an additive effect that is equal to or greater than a sum of the effects of the individual components, and
    wherein the trauma is mechanically-induced metabolic trauma, stress trauma, stress-induced damage, environmental stress, or noise trauma.

2. A method as set forth in claim 1 wherein the step of internally administering the composition is further defined as orally administering the composition to the mammal.

3. A method as set forth in claim 1 wherein the step of internally administering the composition is further defined as intravenously administering the composition to the mammal.

4. A method as set forth in claim 1 wherein the step of internally administering the composition occurs prior to trauma to the middle or inner ear of the mammal.

5. A method as set forth in claim 1 wherein the step of internally administering the composition is further defined as initially internally administering the composition within one day of trauma to the middle or inner ear of the mammal.

6. A method as set forth in claim 5 further comprising the step of internally administering the composition to the mammal each day for at least five days following the trauma to the middle or inner ear of the mammal.

7. A method as set forth in claim 6 wherein an average difference in threshold shift in mammals from baseline threshold sensitivity at 4, 8, and 16 kHz, as compared to an untreated control, is at least 25 decibels when the trauma results from exposure to 120 decibel SPL Octave Band Noise centered at 4 kHz for five hours.

8. A method as set forth in claim 1 wherein the composition further comprises resveratrol.

9. A method as set forth in claim 1 wherein the vitamin A is present in the composition in an amount of at least 830 IU.

10. A method as set forth in claim 1 wherein the vitamin C is present in the composition in an amount of at least 4,000 IU.

11. A method as set forth in claim 1 wherein the vitamin E is further defined as a water-soluble analogue of alpha-tocopheral.

12. A method as set forth in claim 1 wherein the vitamin E is present in the composition in an amount of at least 75 IU.

13. A method as set forth in claim 1 wherein the composition further comprises the withanolide.

14. A method as set forth in claim 1 wherein the vasodilator is present in an amount of at least 50 mg.

15. A method as set forth in claim 1 wherein the trauma is environmental stress.

16. A method as set forth in claim 1 wherein the trauma is noise trauma.

17. A method of treating hearing loss comprising the step of internally administering a composition to a mammal consisting essentially of:
    a biologically effective amount of vitamin A, vitamin E, vitamin C, a vasodilator comprising magnesium, and, optionally, a withanolide, and/or reservatrol,
    wherein the composition is initially administered within three days of trauma to a middle or inner ear of the mammal to provide an additive effect that is equal to or greater than a sum of the effects of the individual components, and
    wherein the trauma is age-related hearing loss, chemotherapeutic-induced hearing loss, metabolic trauma, or hearing loss from restoration surgery performed on the middle or inner ear.

18. A method as set forth in claim 17 wherein the trauma is age-related hearing loss.

19. A method as set forth in claim 17 wherein the trauma is chemotherapeutic-induced hearing loss.

20. A method as set forth in claim 17 wherein the trauma is metabolic trauma.

21. A method as set forth in claim 17 wherein the trauma is hearing loss from restoration surgery performed on the middle or inner ear.

22. A method of treating hearing loss comprising the step of internally administering a composition to a mammal consisting essentially of:

a biologically effective amount of vitamin A, vitamin E, vitamin C, a vasodilator comprising magnesium, and, optionally, a withanolide, and/or reservatrol, wherein the composition is initially administered within three days of trauma to a middle or inner ear of the mammal to provide an additive effect that is equal to or greater than a sum of the effects of the individual components, and wherein the trauma is damage to hair cells within the ear.

* * * * *